United States Patent [19]

Bayol et al.

[11] Patent Number: 5,763,409
[45] Date of Patent: Jun. 9, 1998

[54] STABLE FREEZE-DRIED FORMULATION COMPRISING A PROTEIN ASSAY KIT

[75] Inventors: Alain Bayol, Tournefeuille; Thierry Breul, Montpellier; Patrice Dupin, Ramonville Saint Agne; Philippe Faure, Maurin, all of France

[73] Assignee: Sanofi, Paris, France

[21] Appl. No.: 432,839

[22] Filed: May 2, 1995

[30] Foreign Application Priority Data

May 4, 1994 [FR] France ................... 94 05486

[51] Int. Cl.$^6$ .................. A61K 38/00; A61K 38/43; C07K 14/52
[52] U.S. Cl. .................. 514/21; 514/8; 514/911; 514/970; 530/350; 530/351; 530/397; 530/399; 424/81.5; 424/85.2; 424/94.1; 424/94.3; 424/94.6; 435/810
[58] Field of Search .................. 514/21, 8, 911, 514/970; 530/350, 351, 397, 399; 424/85.1, 85.2, 94.1, 94.3, 94.6; 435/810

[56] References Cited

U.S. PATENT DOCUMENTS

| 5,037,644 | 8/1991 | Saked et al. ............... 424/85.2 |
| 5,096,885 | 3/1992 | Pearlman et al. ............ 514/12 |
| 5,192,743 | 3/1993 | Hsu et al. ................. 514/8 |
| 5,464,614 | 11/1995 | Meyer .................... 424/94.3 |

FOREIGN PATENT DOCUMENTS 2096536  4/1990  Japan.
93/19776 10/1993  WIPO.

OTHER PUBLICATIONS

Schneider et al, *Database WPIDS*, 80–623663; Derwent Information Ltd. (IDD–141996, Sep. 2, 1993 Abstract).
Suenaga et al, *Chemical Abstract*, vol. 80, 1974, p. 265, Ref. No. 124785f. (Japan Kokai, 74–06,115,1(9)74).
Chang et al, *Cryobiology*, vol. 29, pp. 632–656, 1992.
Izutsu et al, *Chemical & Pharmaceutical Bulletin*, vol. 42, No. 1, pp. 5–8, Jan. 1994.
Bontempo et al, *Chemical Abstracts*, vol. 111, 1989, p. 396, Ref. No. 84090a (EP 284, 249, Sep. 28, 1988).
Back et al, *Biochemistry*, vol. 18, No. 23, pp. 5191–5196, 1979.
French Search Report, Jan. 25, 1995.
"Effect of Mannitol Crystallinity on The Stabilisation of Enzymes During Freeze–Drying", K. Izutsu, et al., Chemical & Pharmaceutical Bulletin, vol. 42, No. 1, Jan. 1994, Tokyo.

*Primary Examiner*—Cecilia J. Tsang
*Assistant Examiner*—Abdel A. Mohamed
*Attorney, Agent, or Firm*—Jacobson, Price, Holman & Stern, PLLC

[57] ABSTRACT

A stable, freeze-dried, and pharmaceutically acceptable formulation includes a protein, a buffer, alanine, and mannitol, at a mass ratio of mannitol/alanine being 0.1–1, wherein the formulation being useful in an assay kit.

14 Claims, 5 Drawing Sheets

STABLE FREEZE-DRIED FORMULATION COMPRISING A PROTEIN ASSAY KIT

FIELD OF THE INVENTION

The present invention relates to a pharmaceutically acceptable formulation provided in the form of a freeze-dried product and containing a protein as active ingredient. This formulation is stable at 25° C. and can be reconstituted in liquid form by the addition of a solvent. It can be administered parenterally to humans or to animals or used in an assay kit.

BACKGROUND OF THE INVENTION

It is known that the formulation has a considerable effect on the degradation of proteins during freeze-drying, as well as a high impact on their stability in freeze-dried form. Various formulation variables which affect these parameters are mainly the pH, the quantity of salts present, the type and the quantity of excipients, the type of cryoprotection chosen, as well as the temperatures, pressure and time which are chosen for the freezing, sublimation and desiccation operations. These different variables influence the physical state of the freeze-dried product obtained, namely: vitreous amorphous, soft amorphous, crystalline or a combination of these states.

The role of each of these variables has been studied separately, but their synergistic effect is still poorly elucidated (Pikal M. J. Dellerman K. M., Roy M. L. Riggin M. N., The effects of formulation variables on the stability of freeze-dried Human Growth Hormone, Pharm. Research, 1991, 8, No. 4, 427–436).

A bibliographic revue on the influence of amino acids and polyols on the properties of the solutions to be freeze-dried or of the freeze-dried products has made it possible to draw the following conclusions:

The advantages and disadvantages linked to the presence of amino acids, mannitol, a crystalline phase or an amorphous phase are listed below:

Advantages linked to the presence of amino acids.

It has been demonstrated that the presence of glycine in a freeze-dried product induces crystallization of the molecules present in solution during the freezing stage of the freeze-drying (Korey D. J., Schwartz J. B., Effects of excipients on the crystallization of pharmaceutical compounds during lyophilization, J. Parenteral Sci. Tech., 1989, 43, 2, 80–83). This crystallization of the active ingredient, which is nevertheless not very probable in the case of proteins, makes it possible to enhance its stability.

Alanine, in crystallized form, has the advantage of preventing the collapse of the freeze-dried product during sublimation and desiccation and allows the production of a freeze-dried product with a larger specific surface area and therefore allows a more rapid desiccation (Pikal M. J., Freeze-drying of proteins, Biopharm. 26–30 Oct. 1990).

Disadvantages linked to the presence of amino acids.

The addition of an amino acid to a sugar or to a polyol in a solution to be freeze-dried generally has the effect of decreasing the glass transition temperature of the sugar (te Booy MPWM de Ruiter R A., de Meere A L J., Evaluation of the physical stability of freeze-dried sucrose containing formulations by differential scanning calorimetry, Pharm. Research., 1992, 9, 109–114). Now, a decrease in glass transition temperature is generally synonymous with less stability of a freeze-dried product (Franks F., Freeze-drying; from empiricism to predictability, Cryo-letters, 1990, 11, 93–110).

Advantages linked to the presence of mannitol.

The presence of mannitol in amorphous form surrounding the protein guarantees the presence of noncrystallized water linked to the protein, during freezing, and thereby prevents the denaturation of the protein. Furthermore, the presence of polyols stabilizes the proteins against thermal degradations, through hydrophobic interactions (Back J. F., Oakenfull D., Smith M. B., Increased thermal stability of proteins in the presence of sugars and polyols, Biochemistry, 1979, 18, 23, 5191–96).

Disadvantages linked to the presence of mannitol.

It has been reported that mannitol does not make it possible to preserve the activity of an enzyme at 37° C., contrary to lactose (Ford A. W., Dawson P. J., The effect of carbohydrate additives in, the freeze-drying of alkaline phosphatase, J. Pharm. Pharmacol., 1993, 45 (2), 86–93).

Advantages linked to the presence of a crystalline phase.

The presence of a crystallized solute in a frozen solution, is a means of stabilizing the proteins during desiccation (Carpenter J. F. & Crowe J. H., Modes of stabilization of a protein by organic solutes during desiccation, Cryobiology, 1988, 25, 459–470).

Disadvantages linked to the presence of a crystalline phase.

it has been demonstrated that the loss of activity of a freeze-dried protein is directly linked to the degree of crystallinity of the cryoprotective molecule (Izutsu K. L., Yoshioka S., Terao T., Decreased protein-stabilizing effects of cryoprotectants due to crystallization., Pharm. Research. 1993, 10, No. 8, 1232–1237).

In the formulation of medicinal products containing proteins, the crystallization of excipients should be avoided according to: (Hermansky M., Pesak M., Lyophilization of drugs. VI Amorphous and Cristalline forms Cesk. Farm., 1993, 42, (2), 95–98).

Advantages linked to the presence of an amorphous phase.

The presence of additives in the amorphous state stabilizes the activity of certain enzymes proportionally to the concentration of the additive according to (Izutsu K. L., Yoshioka S., Terao T., Decreased protein-stabilizing effects of cryoprotectants due to crystallization, Pharm. Research. 1993, 10, No. 8, 1232–1237).

The cryoprotective effect of the excipients is attributed to the amorphous state of the glycine in the freeze-dried product obtained (Pikal M. J., Dellermann K. M., Roy M. L. Riggin M. N., The effects of formulation variables on the stability of freeze-dried Human Growth Hormone, Pharm. Research., 1991, 8, No. 4, 427–436).

Disadvantages linked to the presence of an amorphous phase.

In the presence of a solid amorphous phase alone, the freeze-dried product collapses at temperatures greater than the glass transition temperature during freezing.

In a soft amorphous phase, the chemical degradation reactions have much more rapid kinetics than in a crystalline phase.

In conclusion, exhaustive revue of the scientific literature regarding the effect of excipients on the stabilization of proteins makes it possible to find contradictory information on their properties. No theory on the relationships between the structure of a freeze-dried product and its stability is universally accepted. Likewise, the role of polyols and amino acids, alone or in combination, is not described according to a set of generalizable properties, but has been observed with contradictory results according to the proteins studied and the quantities of excipients used.

SUMMARY OF THE INVENTION

A synergistic effect has therefore now been found, quite surprisingly, between mannitol and alanine on the stabilization of freeze-dried proteins. It has been demonstrated that this synergistic effect exists only in a region of relative concentrations of each of these two excipients. The optimum effect is delimited for ratios R, with R representing the mannitol mass/alanine mass present in the freeze-dried product, of between 0.1 and 1, especially 0.2 and 0.8.

Furthermore, it has been demonstrated that for an R of between 0.1 and 1:

The freeze-dried product consists of an amorphous phase and a crystalline phase.

The amorphous phase predominantly consists of mannitol and protein.

The crystalline phase predominantly consists of alanine.

The hypotheses envisaged are that for an R of between 0.1 and 1:

The amorphous phase formed cryoprotects the protein during freezing.

The crystalline phase fixes the structure of the freeze-dried product and avoids its collapse.

It is this surprising synergistic effect between the coexistence of an amorphous phase and a crystalline phase which stabilizes the freeze-dried protein. The present invention therefore describes the production of this effect for preferred R ratios.

Thus, the present invention relates to freeze-dried pharmaceutical dosage forms containing an effective quantity of a biologically active protein, a buffer adjusted to the optimum pH for stability of the protein, alanine and mannitol, the latter two excipients being in a mass ratio R=mass of mannitol/mass of alanine of between 0.1 and 1. The protein included in the said formulation remains stable in freeze-dried form. The dissolution of the freeze-dried product obtained is rapid and complete. The structure of the freeze-dried product is not broken or collapsed and its water content is compatible with the maintenance of the activity of the protein.

Other pharmaceutically acceptable excipients, well known to persons skilled in the art, can be introduced into this formulation, such as for example cosolvents, preservatives, antioxidants or chelating agents.

DETAILED DESCRIPTIONS OF THE INVENTION

The object of the present invention therefore consists in obtaining stable freeze-dried products containing a protein which is cryoprotected by an amorphous solid phase during freezing, consisting essentially of protein and mannitol, this amorphous phase coexisting in the freeze-dried product obtained after sublimation and desiccation of the frozen solution, with a cryatalline phase consisting essentially of alanine.

The biologically active (or bioactive) protein which is formulated according to the present invention may be a glycosylated or nonglycosylated, natural, synthetic, semisynthetic or recombinant polypeptide as used in clinical or laboratory practice More particularly, the said protein may be for example a hormone such as a growth hormone, preferably human growth hormone (hGE), a luteinizing hormone (LH-RH), a gonadotrophin. The protein may also be an enzyme, for example a thrombolytic enzyme such as a urokinase, a prourokinase, a streptokinase, a staphilokinase, a tissue plasminogen activator (tPA) or an enzyme such as a phosphatase, a sulphatase, an acyltransferase, a monoamine oxidase, a urate oxidase. Likewise, a protein which is formulated according to the present invention may be a cytokine, such as for example interleukin-2 (IL-2), interleukin-4 (IL-4), interleukin-6 (IL-6) or interleukin-13 (IL-13). Another class of proteins according to the present invention includes for example antibodies, immunoglobulins, immunotoxins. Peptides such as cholecystokinin (CCK), substance P, neurokinin A, neurokinin B, neurotensin, neuropeptide Y, eledoisin, bombesin can be formulated according to the present invention.

The biologically active protein is preferably hGH (or human growth hormone), urate oxidase or interleukin-13.

Human growth hormone is a protein consisting of a single polypeptide chain of 191 amino acids with 2 disulphide bridges between the cystein residues 53 and 165 and the cystein residues 182 and 189.

Urate oxidase is an enzyme which oxidizes uric acid into allantoin and is extracted from the biomass of *Aspergillus flavus* (Laboureur et al., Bull. Soc. Chim. Biol. 1968, 50, 811–825). It has been used for the treatment of hyperuricemias for more than 20 years.

The cDNA encoding this protein has been recently cloned and expressed in *E. coli* (LEGOUX R et al., J. of Biol. Chem., 1992, 267, 12, 8565–8570), *Aspergillus flavus* and *Saccharomyces cerevisiae*. The enzyme is a tetramer with identical subunits of molecular mass in the region of 32,000. The monomer, consisting of a single polypeptide chain of 301 amino acids, has no disulphide bridges and is acetylated at the N-terminal end.

Interleukin-13 is a cytokin consisting of a single polypeptide chain of 112 amino acids with two disulphide bridges (Minty et al., Nature, 1993, 362, 248–250).

The obtaining of the coexistence of the amorphous (mannitol+protein) phase with the crystalline alanine phase is independent of the presence and of the concentration of a buffer for adjusting the pH of the solution, but it depends on the R ratio defined above.

In order to propose protein formulations which are available to the public as therapeutic agents, it is essential to formulate them in a sufficiently stable form so as to maintain their biological activity between the time of the formulation and that of use. For example, hGH has been formulated in various ways such as those described in the following patents or patent applications: U.S. Pat. No. 5,096,885; WO 89/09614; WO 92/17200, Au-30771/89; WO 93/19773; WO 93/19776.

The formulations according to the invention can be preserved at room temperature, whereas currently marketed formulations containing these proteins must be preserved at temperatures of 2° C. to 8° C.

In most cases, the pharmaceutical dosage form is freeze-dried, frozen, or in solution. It contains the protein, a buffer, glycine, arginine, mannitol, zinc, surfactants, dextran, EDTA, or other excipients but never the combination alanine/mannitol in a mass ratio R of between 0.1 and 1. The freeze-dried or frozen forms are used to maintain the biochemical integrity and the biological activity of the molecule. The freeze-dried formulations should be reconstituted before use by addition of pharmaceutically acceptable sterile solvents such as distilled water, aqueous solutions of sodium chloride at 0.9% or of glucose at 5% or any other physiologically acceptable solvent, containing or otherwise antibacterial preservatives such as benzyl alcohol, phenol or metacresol.

A formulation which is stable at room temperature until it is reconstituted is particularly advantageous for an ambulatory treatment as in the case of hGH in the form of a bottle or a presentation adapted in the form of a multidose pen.

The formulation thus prepared can also be introduced into an assay kit.

The present invention is therefore a preferred composition of a freeze-dried product. This freeze-dried product is obtained by freeze-drying starting with a solution.

The process of this formulation includes steps of mixing, dissolving, filtering and freeze-drying. The composition of the solution to be freeze-dried is the following:

A protein, a pharmaceutically acceptable buffer to adjust the pH, alanine, mannitol where the mass ratio R=mass of mannitol/mass of alanine is between 0.1 and 1, water for injection.

The Solution to be Freeze-Dried is Prepared in the Following Manner:

The protein solution is obtained on a gel filtration column and contains a buffer which maintains its pH in a zone compatible with the stability of the protein.

The desired quantities of buffer, alanine, mannitol and water are added to this solution so as to solubilize all the excipients. The solution is sterilely filtered and distributed into containers, preferably vials or carpules.

The Freeze-Drying of the Solutions is Carried Out As Follows:

The solution follows a cycle of freezing, then sublimation and desiccation which is adapted to the volume to be freeze-dried and to the container containing the solution. Preferably, a freezing rate of close to −2° C./min is chosen in a Usifroid freeze-drier (France) of the SMH15 or SMJ100 or SMH2000 type.

The time, temperature and pressure of desiccation of the freeze-dried product are adjusted as a function of the volumes of solution to be freeze-dried and the desired residual water content in the freeze-dried product.

Complete information on the techniques for preparing the injectable formulations is available to persons skilled in the art in Remington's Pharmaceutical Sciences, 1985, 17th Edition or in William N A & Polli G P. The lyophilization of pharmaceuticals: a literature review, J. Parenteral Sci. Tech., 1984, 38, (2), 48–59 or in Franks F., Freeze-drying: from empiricism to predictability, Cryo-letters, 1990, 11, 93–110.

A freeze-dried product is thereby obtained in which alanine is in crystallized form and mannitol is in amorphous form. The freeze-dried product can be preserved at 25° C. without impairing the biological activity of the protein which it contains.

To illustrate the present invention, evaluations were made choosing hGH or urate oxidase as an example of protein. Thus, several solutions containing hGH or urate oxidase as biologically active protein, a phosphate buffer at various concentrations, at pH=7 for the solutions containing hGH (at 4 IU/0.5 ml), and pH=8 for those containing urate oxidase (at 30 EAU/ml, mannitol alone, alanine alone, or alanine/mannitol mixtures) were prepared, freeze-dried and analysed.

The compositions are described in detail in the examples of TABLES 1 and 2 below. The methods of analysis as well as the stabilizing times and temperatures are also described below.

TABLE 1

TABLE 1 below indicates the compositions of the urate oxidase-containing formulae studied.

| Batch No. | mg Mannitol | mg Alanine | R | Phosphate buffer pH = 8; mM | Urate oxidase EAU[(i)] |
|---|---|---|---|---|---|
| 1 | 33.0 | 0.0 | + ∞ | 50 | 30 |
| 2 | 27.7 | 6.9 | 4 | 30 | 30 |
| 3 | 20.8 | 10.4 | 2 | 30 | 30 |
| 4 | 13.6 | 13.6 | 1.000 | 40 | 30 |
| 5 | 10.2 | 15.3 | 0.67 | 40 | 30 |
| 6 | 7.3 | 16.0 | 0.46 | 40 | 30 |
| 7 | 7.3 | 16.2 | 0.45 | 30 | 30 |
| 8 | 9.5 | 21.0 | 0.45 | 50 | 30 |
| 9 | 4.6 | 18.3 | 0.25 | 40 | 30 |
| 10 | 2.5 | 20.0 | 0.125 | 40 | 30 |
| 11 | 0.0 | 16.0 | 0 | 50 | 30 |

[(i)]: EAU means enzyme activity unit

TABLE 2

TABLE 2 below indicates the composition of the hGK-containing formulae studied

| Batch No. | mg Mannitol | mg Alanine | R | Phosphate buffer pH = 7; mM | hGH IU[(i)] |
|---|---|---|---|---|---|
| 12 | 12.5 | 0.0 | + ∞ | 2.50 | 4 |
| 13 | 20.0 | 2.5 | 8 | 1.95 | 4 |
| 14 | 12.5 | 2.5 | 2 | 0.00 | 4 |
| 15 | 12.5 | 6.5 | 2 | 2.50 | 4 |
| 16 | 12.5 | 13.0 | 1 | 2.50 | 4 |
| 17 | 4.7 | 10.5 | 0.45 | 1.95 | 4 |
| 18 | 0.0 | 6.5 | 0 | 2.50 | 4 |

[(i)]: IU: international unit

The analytical methods which were used for the determination of the different parameters are the following.

Contents of dimers and related substances of higher Molecular Mass:

The content of dimers and related substances of higher molecular mass is determined by exclusion chromatography (SEC-HPLC) using a SUPEROSE 12 column (Pharmacia, Ref. 17-0538-01). The product is eluted with an ammonium phosphate buffer Solution at pH=7.0 (1.38 g of ammonium dihydrogen phosphate in 1 litre of water, adjusted to pH=7.0 with concentrated ammonium hydroxide at a flow rate of 0.4 ml/minute). The detection is carried out at 220 nm. (This content is noted in the analytical results as percentages of oligomers +polymers).

The content of dimers and substances of higher molecular mass can also be determined by the method described in the European Pharmacopoeia monograph "Somatropine pour preparation injectable" (Somatropin for injectable preparation) of January 1994.

Assay of the Protein Titre by Reversed-Phase Chromatography.

Expressed in mg per vial, it is determined by reversed-phase chromatography using a C18—300 Å column—25 cm, diameter 4.6 mm (SYNCHROM, ref. CR103-25). The product is eluted in 35 minutes in gradient mode with a mobile phase passing from 75 volumes of water at 0.1% trifluoroacetic acid (V/V) (TFA) and 25 volumes of acetonitrile at 0.08% TFA (V/V) to 30 volumes of water at 0.1% TFA and 70 volumes of acetonitrile at 0.08% TFA. The flow rate is 1 ml per minute and the detection is carried out at 220 nm Assay of the Enzymatic Activity of Urate Oxidase.

The enzymatic activity of urate oxidase expressed as EAU is determined by spectrophotometry in a thermostated cuvette at 30° C. by monitoring the disappearance of uric acid at 292 nm according to Legoux R, Delpech Bruno, Dumont X, Guillemot J. C., Ramond P, Shire D, Caput D, Ferrara P, Loison G, J. Biol. Chem. 1992, 267 (12), 8565–8570.

Turbidity of the Reconstituted Solutions.

The turbidity of the hGH-containing freeze-dried products taken up in solution is determined by spectrophotometry (Ph. Eur. 2 (I) V.619) at 500 nm in a Perkin Elmer 554 spectrophotometer. The results are provided in Absorbance Units×1000.

The turbidity of the urate oxidase-containing freeze-dried products taken up in solution is determined with the aid of a Ratio Hach 18900-00 turbidimeter. The turbidity results are expressed in Nephelometric Turbidity units (NTU) defined by: Standard methods for the examination of water and wastewater of the American Public Health Association.

The degree of opalescence is also determined according to the method of the European Pharmacopoeia (II) V. 6, by comparing the sample to be analysed with a control suspension.

Organoleptic Criteria for the Freeze-Dried Products.

These criteria are examined visually and take into account the colour of the freeze-dried product, its structure (collapsed or otherwise), and the observation of a possible phase shift between the crust and the crumb of the freeze-dried product.

X-Ray diffractometry on Powder.

X-ray diffractometric analysis on the freeze-dried products is carried out in a SIEMENS D500 TT diffractometer; source: CuKα1; generator: 40 KV, 25 mA; back monochromator; slit: 1/1/1/0.16/0.6; sampling on a Pyrex rack; scanning region: 4° to 40° per minute in 2 Bragg theta.

Differential Thermal Analysis.

The study of the freeze-dried products by differential thermal analysis is carried out under the following conditions:

Apparatus: DSC 7 Perkin Elmer; calibration: indium and lead; sample size: between 5 mg and 10 mg in a 50 μl dish; initial temperature: 10° C.; rate of heating 10° C./minute; final temperature: 300° C.

Deamidated Forms of hGH.

The percentage of deamidated forms is determined by anion-exchange chromatography (AEX-HPLC) using an anion-exchange column (PHARMACIA mono-Q HR 5/5, ref. 17-0546-01). The elution is performed with a solution A (13.8 g of ammonium dihydrogen phosphate in 1000 ml of water; pH=7 adjusted with concentrated ammonium hydroxide) and water as solution B, using the following programming: 5% of solution A for 2 minutes, then passage to 15% of solution A over 5 minutes, then passage to 50% of solution A over 20 minutes, finally passage to 100% of solution A over 5 minutes and maintenance of the latter solution for 5 minutes. The elution of hGH ($t_R$ about 15 minutes) and of the deamidated forms is monitored at 220 nm. The flow rate is 1 ml per minute.

The analytical results obtained using these different methods are described below.

Content of Dimers and Related Substances of Higher Molecular Mass

Figure 1:
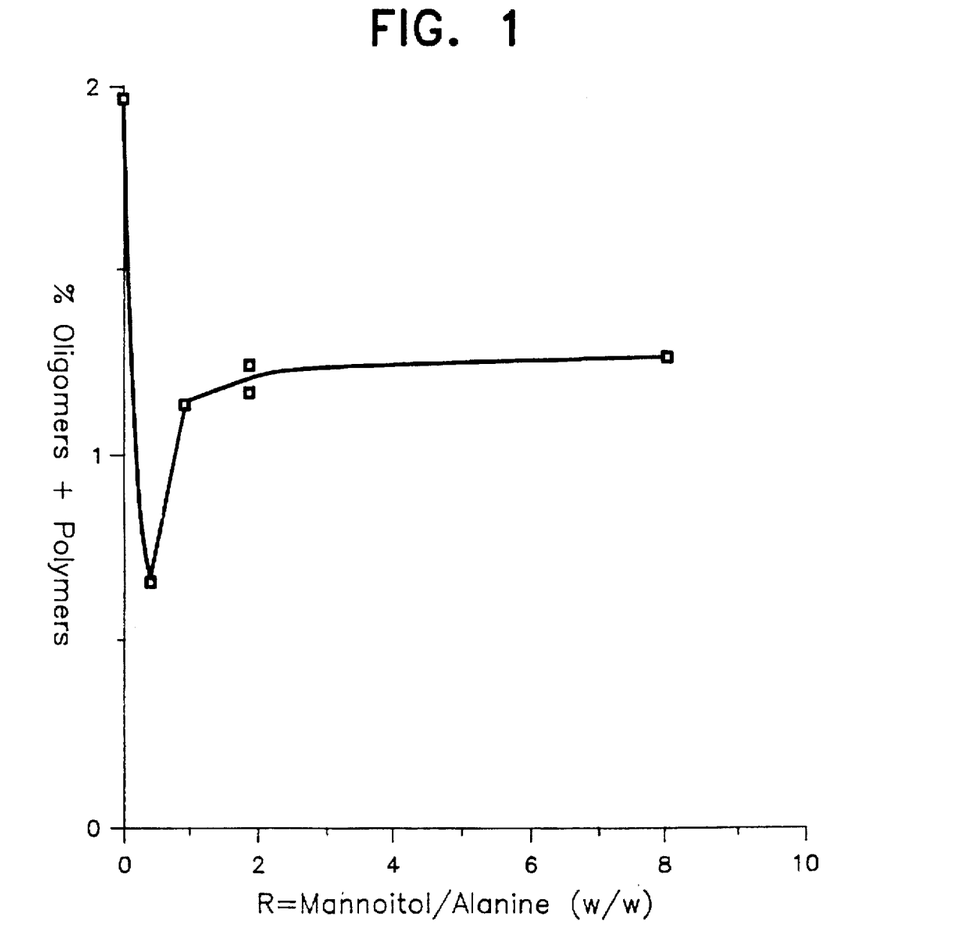
FIG. 1 is a graph that shows up-take of materials as a function of the mannitol/alanine ratio.

The content of oligomers plus polymers of the freeze-dried products containing 4 IU of hGH taken up in 0.5 ml o:E water was determined as a function of the R ratio (FIG. 1). FIG. 1 indicates that the minimum content of oligomers plus polymers of the solutions is obtained for an R of between 0.1 and 1, the value 0.1 being interpolated from the curve.

By way of additional example, two batches of hGH at 4 IU and 8 IU were monitored for stability at 25° C. and 35° C. Their stability is excellent after 6 months of preservation.

TABLES 3 and 4 below indicate the percentages of oligomers and polymers of deamidated forms at different times and temperatures compared with the European Pharmacopoeia standards. In these tables, R=0.45.

TABLE 3

| | Batch 4 IU per vial | | | | |
|---|---|---|---|---|---|
| | European Pharmacopoeia | | at 25° C. | at 35° C. | |
| | Standard | Time 0 | 3 months | 3 months | 6 months |
| Oligomers and polymers in % | 6.0 | 1.0 | 1.9 | 3 | 3.3 |
| Deamidated forms in % | 6.6 | 1.3 | 1.9 | 2.8 | 3.9 |
| Assay in mg per vial | — | 1.58(*) | 1.61(*) | 1.54(*) | 1.55(*) |

(*): The titre does not vary significantly over time given the precision of the assay method (± 5%)

TABLE 4

| | Batch 8 IU per vial | | | | |
|---|---|---|---|---|---|
| | European Pharmacopoeia | | at 25° C. | | at 35° C. |
| | Standard | Time 0 | 3 months | 6 months | 3 months | 6 months |
| Oligomers and polymers in % | 6 | 1.0 | 1.5 | 1.2 | 1.7 | 2.2 |
| Deamidated forms in % | 6.6 | 1.0 | 1.5 | 1.95 | 2.2 | 3.3 |

TABLE 4-continued

| | European Pharmacopoeia Standard | Batch 8 IU per vial | | | |
|---|---|---|---|---|---|
| | | | at 25° C. | | at 35° C. |
| | | Time 0 | 3 months | 6 months | 3 months | 6 months |
| Assay in mg per vial | — | 3.0(*) | 3.0(*) | 2.93(*) | 2.95(*) | 2.94(*) |

(*): The titre does not vary significantly over time given the precision of the assay method (± 5%)

Assay of the Enzymatic Activity of Urate Oxidase.

Figure 2:
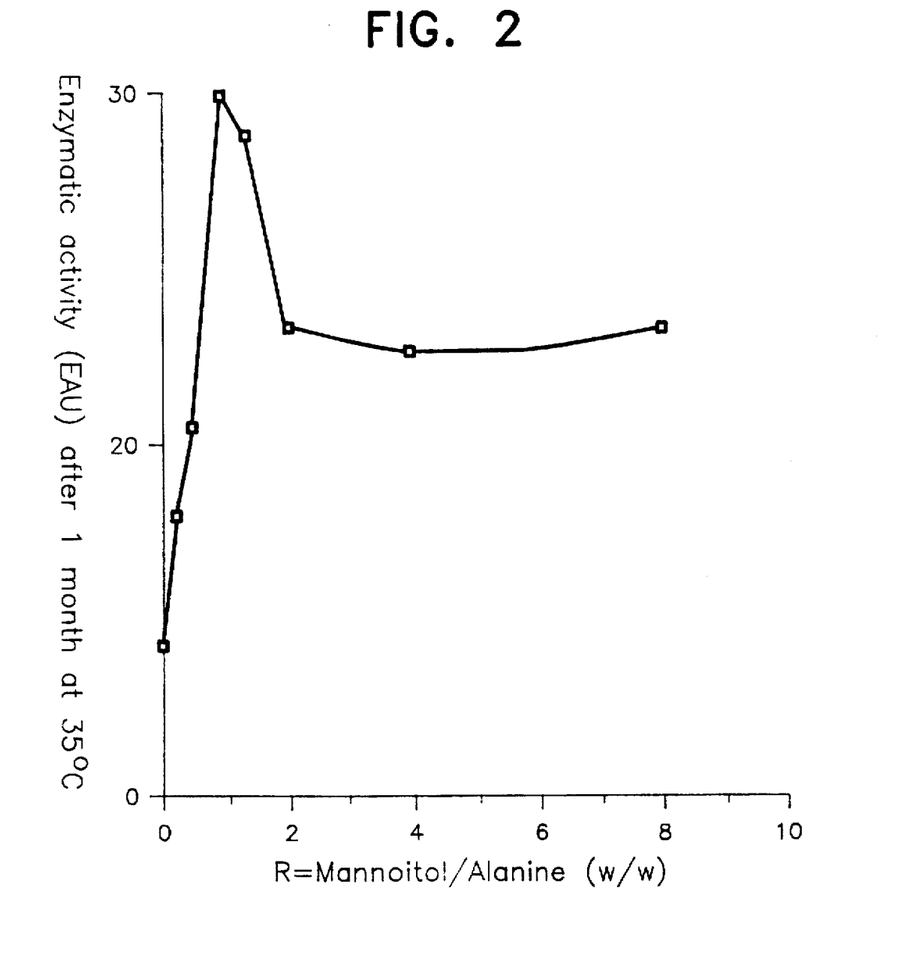
FIG. 2 is a graph that shows enzymatic activity of materials as a function of the mannitol/alanine ratio.

The enzymatic activity of the freeze-dried products containing 30 EAU of urate oxidase taken up in 1 ml of water was determined as a function of the R ratio after 1 month at 35° C. (cf. FIG. 2). FIG. 2 indicates that the initial enzymatic activity of urate oxidase is preserved after 1 month at 35° C. for an R of between 0.4 and 1.

By way of additional example, a formula with R=0.45 or R=0.67 is perfectly stable after 3 months at 25° C. (residual activity close to 100% of that of time zero).

Turbidity of the Reconstituted Solution.

Figure 3:
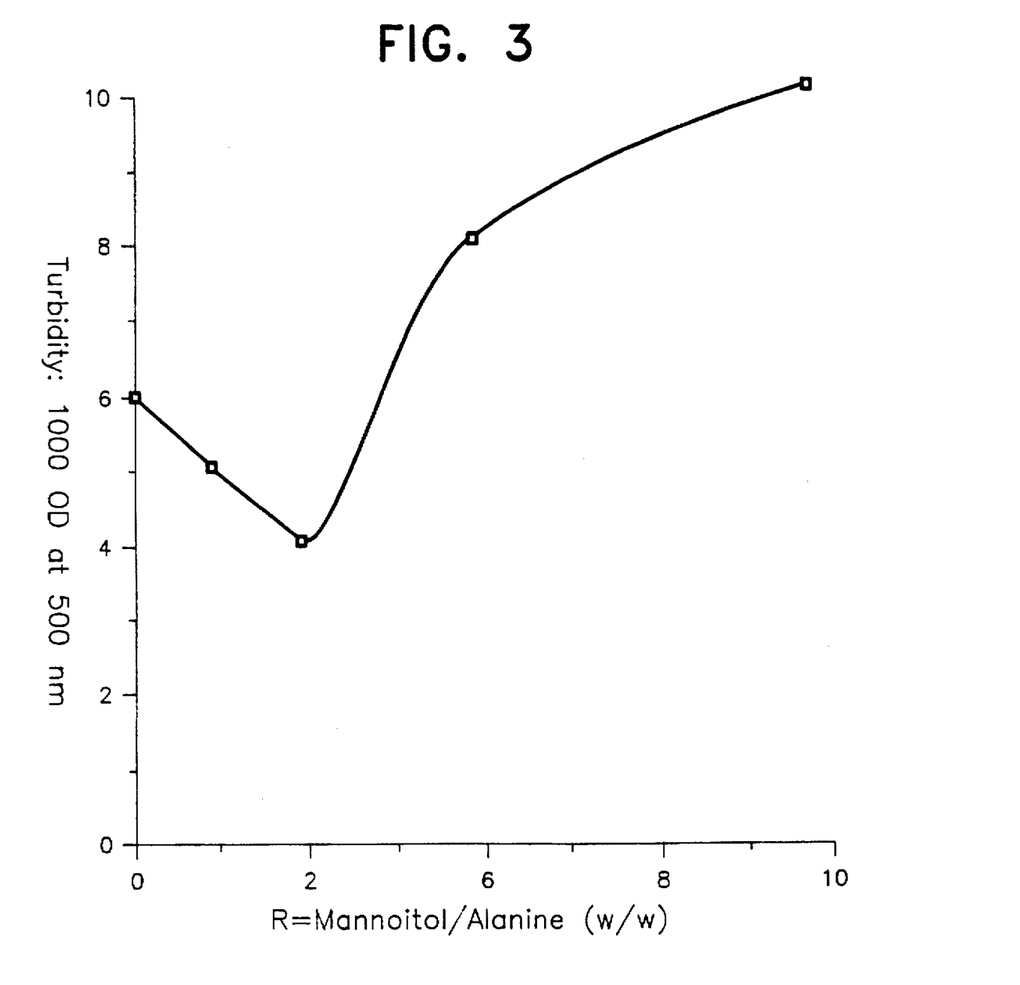
FIG. 3 is a graph that shows turbidity (1000 OD at 500 nm) of materials as a function of the mannitol/alanine ratio.

The turbidity of the freeze-dried products containing 4 IU of hGH taken up in 0.5 ml of water was determined as a function of the R ratio (cf. FIG. 3). FIG. 3 indicates that the minimum turbidity of the solutions is obtained for an R of between 0 and 1.5.

Figure 4:
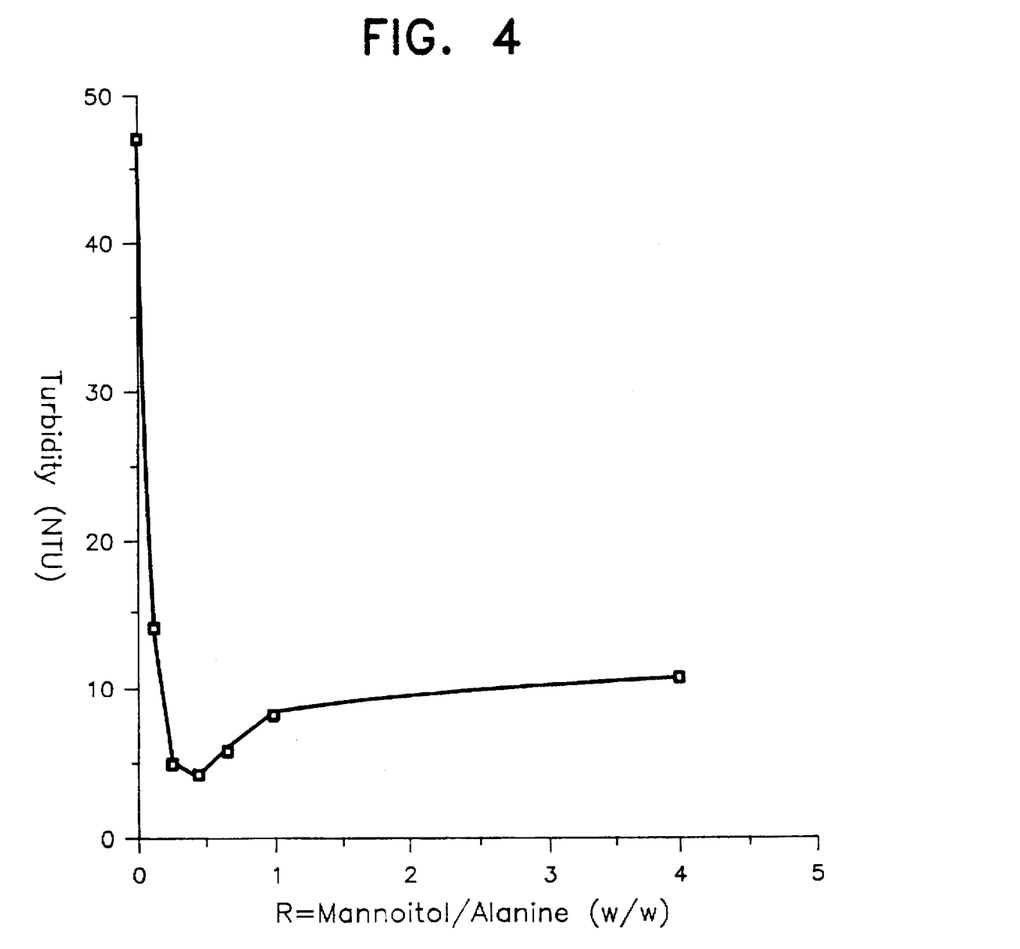
FIG. 4 is a graph that shows turbidity (NTU) of materials as a function of the mannitol/alanine ratio.

The turbidity of the freeze-dried products containing 30 EAU of urate oxidase taken up in 1 ml of water was determined as a function of the R ratio (cf. FIG. 4). FIG. 4 indicates that the minimum turbidity obtained on the solutions is obtained for an R of between 0.2 and 1.

Organoleptic Criteria for the Freeze-Dried Products.

The organoleptic criteria for each freeze-dried product containing 4 IU of hGH or 30 EAU of urate oxidase or no protein, and various contents of phosphate buffer were determined as a function of the R ratio, and are provided in TABLE 5. TABLE 5 indicates that the freeze-dried products exhibit satisfactory organoleptic criteria for an R of between 0.125 and 1.7.

These characteristics do not vary as a function of time.

TABLE 5

Organoleptic criteria for the freeze-dried products and crystallized excipients as a function of the ratio
R = mass of mannitol/mass of alanine

| R | Organoleptic criteria | Crystalline excipients (X-ray diffraction) |
|---|---|---|
| + ∞ | Broken (or collapsed) | Mannitol |
| 10 | Broken (or collapsed) | Mannitol + Alanine |
| 6.469 | Broken (or collapsed) | Mannitol + Alanine |
| 5 | Broken (or collapsed) | Mannitol + Alanine |
| 4.014 | Broken (or collapsed) | Mannitol + Alanine |
| 2 | Broken (or collapsed) | Mannitol + Alanine |
| 1.705 | Good | Mannitol + Alanine |
| 1.402 | Good | Mannitol + Alanine |
| 1.25 | Good | Mannitol + Alanine |
| 1.097 | Good | Mannitol + Alanine |
| 1 | Good | Alanine |
| 0.667 | Good | Alanine |
| 0.456 | Good | Alanine |
| 0.456 | Good | Alanine |
| 0.451 | Good | Alanine |
| 0.452 | Good | Alanine |
| 0.251 | Good | Alanine |
| 0.125 | Good | Alanine |

TABLE 5-continued

Organoleptic criteria for the freeze-dried products and crystallized excipients as a function of the ratio
R = mass of mannitol/mass of alanine

| R | Organoleptic criteria | Crystalline excipients (X-ray diffraction) |
|---|---|---|
| 0 | Phase shift (or separation) | Alanine |

X-Ray Diffraction.

The results of the X-ray diffraction analysis on the powder of the freeze-dried products obtained containing Alanine/Mannitol mixtures in R ratios varying from 0 to + ∞ are provided in TABLE 5.

The diffractograms obtained show that for an R of between 0 and 1, only the lines of the alanine crystalline lattice appear; furthermore, the deviation from the base line of the diffractogram indicates the presence of an amorphous phase consisting of mannitol. The greater R, the greater the amorphous phase due to mannitol. For R>1, the mannitol also crystallizes.

An amorphous phase is obtained consisting of mannitol and a crystalline phase consisting of alanine for an R of between 0 and 1.

Differential Thermal Analysis.

Figure 5:
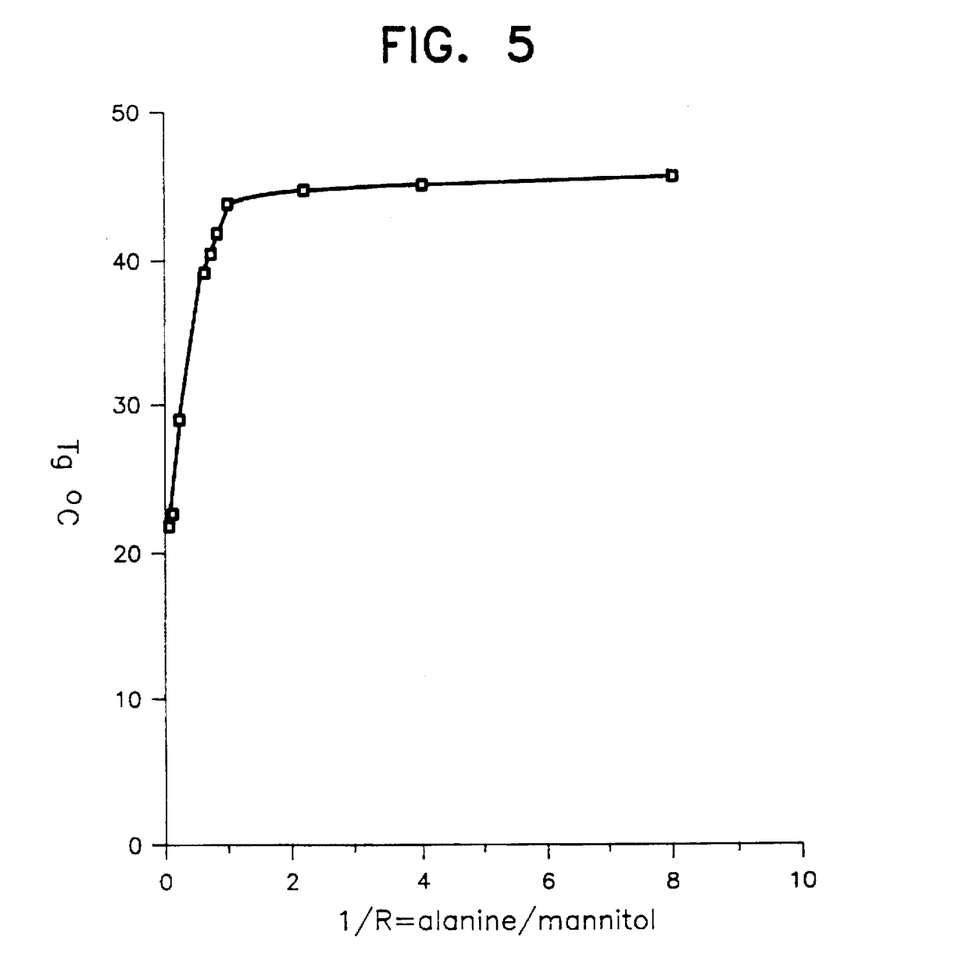
FIG. 5 is a graph that shows glass transmission temperature ($T_g$) of materials as a function of (reciprocal ratio) 1/R=alanine/mannitol.

The glass transition temperatures of the freeze-dried products containing 4 IU of hGH or 30 EAU of urate oxidase or no protein, and various contents of phosphate buffers were determined as a function of the reciprocal of the R ratio (cf. FIG. 5). FIG. 5 indicates that the maximum glass transition temperature obtained on the freeze-dried products containing mixtures of alanine and mannitol is obtained for (1/R)>1, that is to say for an R of between 0 and 1.

It is the glass transition temperature of the freeze-dried product which indicates the maximum temperature of stability of the freeze-dried product. The maximum temperature of stability of the freeze-dried product is therefore reached for an R of between 0 and 1.

Deamidated Forms

The results obtained on the 4 IU and 8 IU batches show only a very small variation-which is very acceptable compared with the standards for the somatropin monograph of the European Pharmacopoeia. They make it possible to think that this formula will be sufficiently stable at 25° C.

In conclusion, it has been proved that each property evaluated on the freeze-dried products exhibits an optimum for an interval of R value which can be summarized in the following manner:

| | |
|---|---|
| % Oligomers + Polymers (hGH stability) | R between 0.1 and 1 |
| Enzymatic activity of urate oxidase after 1 | R between 0.4 and 1 |

-continued

| | |
|---|---|
| month at 35° C. | |
| Turbidity hGH solutions | R between 0 and 1.5 |
| Turbidity urate oxidase solutions | R between 0.2 and 1 |
| Appearance of the freeze-dried products | R between 0.125 and 1.7 |
| Alanine alone crystalline | R between 0 and 1 |
| Maximum glass transition temperature | R between 0 and 1 |

Each analytical criterion (% oligomers+polymers, hGH stability, enzymatic activity of urate oxidase after 1 month at 35° C., turbidity hGH solutions, turbidity urate oxidase solutions, appearance of the freeze-dried products, alanine alone crystalline, maximum glass transition temperature) defines a specific optimum interval per property. To obtain an acceptable formulation, a preferred interval of R is defined, that in to say $0.1<R<1$.

The following EXAMPLES illustrate the invention without however limiting it.

EXAMPLE 1:
Composition of a freeze-dried product of hGH at 4 IU to be taken up in 0.5 ml of water for injection

| CONSTITUENTS | Unit formula in (mg) |
|---|---|
| hGH | 4 IU |
| Alanine | 10.5 mg |
| Mannitol | 4.77 mg |
| Disodium phosphate dodecahydrate | 0.7 mg |
| Water for injection | qs 0.5 ml |
| Type 1 white glass vial of 3 ml | 1 |
| Grey chlorobutyl pillar stopper | 1 |
| Blue Flip-off alu dish diameter 13 mm | 1 |

EXAMPLE 2:
Composition of a freeze-dried product of hGH at 8 IU to be taken up in 1 ml of water for injection

| CONSTITUENTS | Unit formula in (mg) |
|---|---|
| hGH | 8 IU |
| Alanine | 21 mg |
| Mannitol | 9.54 mg |
| Disodium phosphate dodecahydrate | 1.4 mg |
| Water for injection | qs 1 ml |
| Type 1 white glass vial of 3 ml | 1 |
| Grey chlorobutyl pillar stopper | 1 |
| Blue Flip-off alu dish diameter 13 mm | 1 |

EXAMPLE 3:
Composition of a freeze-dried product of hGH at 18 IU to be taken up in 1 ml of water for injection

| CONSTITUENTS | Unit formula in (mg) |
|---|---|
| hGH | 18 IU |
| Alanine | 21 mg |
| Mannitol | 9.54 mg |
| Disodium phosphate dodecahydrate | 1.4 mg |
| Water for injection | qs 1. ml |
| Type 1 white glass vial of 3 ml | 1 |
| Grey chlorobutyl pillar stopper, diameter 13 mm | 1 |
| Blue Flip-off alu dish diameter 13 mm | 1 |

EXAMPLE 4:
Freeze-dried products of hGH for injection at 8 IU in 1 ml

| Nature of the controls | Methods used | Standards | TEMPERATURE in °C. x DURATION IN DAYS 0 Results | 5 90 Results | 25 90 Results | 35 90 Results | 5 180 Results | 25 180 Results | 35 180 Results |
|---|---|---|---|---|---|---|---|---|---|
| CHARACTERISTICS | | | | | | | | | |
| Appearance | in conformity | | in conformity | in conformity | in conformity | in conformity | in conformity | in conformity | in conformity |
| IDENTIFICATION | | | | | | | | | |
| hGH | Reversed phase | in conformity | in conformity | in conformity | in conformity | in conformity | in conformity | in conformity | in conformity |
| | Exclusion chromatography | in conformity | in conformity | in conformity | in conformity | in conformity | in conformity | in conformity | in conformity |
| TEST | | | | | | | | | |
| Deamidated forms | Anion exchange | <6.5% | 1.0% | 1.0% | 1.5% | 2.2% | 1.5% | 1.95% | 3.3% |
| Dimers and related substances | Exclusion chromatography | <6.0% | 1.0% | 0.75% | 1.5% | 1.7% | 0.8% | 1.2% | 2.2% |
| Cut forms | Electrophoresis | <2.0% | <2.0% | <2.0% | <2.0% | <2.0% | <2.0% | <2.0% | <2.0% |
| Related proteins | Electrophoresis | in conformity[1] | in conformity | in conformity | in conformity | in conformity | in conformity | in conformity | in conformity |
| Water content | | <1.5% | 0.45 | 0.41 | 0.68 | 0.73 | 0.47 | n.s.[2] | n.s.[2] |
| ASSAY in mg/vial RECONSTITUTED | Reversed phase | 2.93 to 3.24 | 3.0 | 3.1 | 3.0 | 2.95 | 2.96 | 2.93 | 2.94 |

EXAMPLE 4:
Freeze-dried products of hGH for injection at 8 IU in 1 ml

SOLUTION

| TEST APPEARANCE | European pharmacopoeia | <susp. II | | <susp. II | <susp. II | <susp. II | <susp. II |
|---|---|---|---|---|---|---|---|
| | European pharmacopoeia | Colourless | | colourless | colourless | colourless | colourless |
| | Determination of the pH | 6.5 to 7.5 | | 6.94 | 7.02 | 7.03 | 7.01 |
| | Dissolution | <1 min | | <1 min | <1 min | <1 min | <1 min |

[1] Absence of additional bands other then artifactual traces present in the control or traces of oligomers of hGH.
[2] n.s. = not studied

EXAMPLE 5:
Freeze-dried product of hGH for injection at 4 IU in 0.5 ml

| Nature of the controls | | TEMPERATURE IN °C. | x | 5 | 25 | 35 | 5 | 35 |
|---|---|---|---|---|---|---|---|---|
| | | DURATION IN DAYS | 0 | 90 | 90 | 90 | 180 | 180 |
| | Methods used | Standards | Results | Results | Results | Results | Results | Results |
| CHARACTERISTICS | | | | | | | | |
| Appearance | | in conformity | in conformity | in conformity | in conformity | in conformity | in conformity | in conformity |
| IDENTIFICATION | | | | | | | | |
| hGH | Reversed phase | in conformity | in conformity | in conformity | in conformity | in conformity | in conformity | in conformity |
| | Exclusion chromatography | in conformity | in conformity | in conformity | in conformity | in conformity | in conformity | in conformity |
| TEST | | | | | | | | |
| Deamidated forms | Anion exchange | <6.5% | 1.3% | 1.0% | 1.9% | 2.8% | 1.3% | 3.9% |
| Dimers and related substances | Exclusion chromatography | <6.0% | 1.0% | 0.6% | 1.9% | 3.0% | 1.0% | 3.3% |
| Cut forms | Electrophoresis | <2.0% | <2.0% | <2.0% | <2.0% | <2.0% | <2.0% | <2.0% |
| Related proteins | Electrophoresis | in conformity[1] | in conformity | in conformity | in conformity | in conformity | in conformity | in conformity |
| Water content | | <1.5% | 0.65 | 0.58 | 0.97 | 0.93 | 0.81 | n.s.[2] |
| ASSAY in mg/vial | Reversed phase | 1.50 to 1.70 | 1.58 | 1.57 | 1.61 | 1.54 | 1.56 | 1.55 |
| RECONSTITUTED SOLUTION | | | | | | | | |
| TEST APPEARANCE | European pharmacopoeia | <susp. II | <susp. II | <susp. II | <susp. II | <susp. II | <susp. II | <susp. II |
| | European pharmacopoeia | Colourless | Colourless | Colourless | Colourless | Colourless | Colourless | Colourless |
| | Determination of th pH | 6.5 to 7.5 | 7.01 | 7.22 | 6.96 | 6.99 | 7.06 | 7.00 |
| | Dissolution | <1 min | <1 min | <1 min | <1 min | <1 min | <1 min | <1 min |

[1] Absence of additional bands other then artifactual traces present in the control or traces of oligomers of hGH.
[2] n.s. = not studied

EXAMPLE 6:
Analytical results after 1 year of stability at 5° C. of hGH at 18 IU

| | Opalescences (A.U. × $10^{-3}$) | pH | Water content | Deamidated forms | Oligomers + polymers |
|---|---|---|---|---|---|
| Standards | <20 | | <1.5% | <5% | <6% |
| t = 0 | 1 | 7.9 | 0.33% | 1.36% | 0.63% |
| 1 month | 1 | 8 | 0.29% | — | — |
| 3 months | 3 | 7.23 | 0.32% | 1.25% | 0.45% |
| 6 months | 4 | — | 1.03% | 1.4% | 0.5% |
| 12 months | 7 | — | 1.19% | 1.15% | 1.11% |

For the entire results, R = 0.45

EXAMPLE 7:
Analytical results after 3 months of stability at 25° C. of hGH at 18 IU

| | Opalescences (A.U. × $10^{-3}$) | pH | Water content | Deamidated forms | Oligomers + polymers |
|---|---|---|---|---|---|
| Standards | <20 | | <1.5% | <5% | <6% |
| t = 0 | 1 | 7.9 | 0.33% | 1.36% | 0.63% |
| 1 month | 3 | 7.72 | 0.35% | — | — |
| 3 months | 9 | 7.65 | 0.54% | 1.37% | 0.85% |

For the entire results, R = 0.45

EXAMPLE 8:
Composition of the freeze-dried products of urate oxidase at 30 EAU/vial

| | RECONSTITUTED SOLUTIONS | | | | | | | |
|---|---|---|---|---|---|---|---|---|
| | CLARITY European Pharmacopoeia | | | | COLOUR European Pharmacopoeia | | | |
| | | 1 month | 3 months | | | 1 month | 3 months | |
| COMPOSITION | t = 0 | 35° C. | 5° C. | 25° C. | t = 0 | 35° C. | 5° C. | 25° C. |
| Mannitol 7.3 mg + L Alanine 16.2 mg Na$_2$HPO$_4$ 30 mM | < = II | < = II | I–II | II–III | colourless | colourless | colour-less | colourless |
| Mannitol 20.8 mg + L Alanine 10.4 mg Na$_2$HPO$_4$ 30 mM | <I | > = III | <II | III–IV | colourless | colourless | colourless | colourless |
| Mannitol 27.7 mg + L Alanine 6.9 mg Na$_2$HPO$_4$ 21 mM | <III | >IV | *III | >IV | colourless | colourless | colourless | colourless |

| | pH of the reconstituted solution | | | | ENZYMATIC ACTIVITY EAU/vial | | | | |
|---|---|---|---|---|---|---|---|---|---|
| | | 1 month | 3 months | | | 1 month | 3 months | | WATER CONTENT |
| COMPOSITIONS | t = 0 | 35° C. | 5° C. | 25° C. | t = 0 | 35° C. | 5° C. | 25° C. | IN % |
| Mannitol 7.3 mg + L Alanine 16.2 mg Na$_2$HPO$_4$ 30 mM | 7.96 | 7.96 | 7.91 | 7.93 | 32.9(*) | 30.0(*) | 30.2(*) | 33.3(*) | 3.2 |
| Mannitol 20.8 mg + L Alanine 10.4 mg Na$_2$HPO$_4$ 30 mM | 8.03 | 8.05 | 8.01 | 8.01 | 28.1(*) | 22.5 | 32.0(*) | 22.7 | 2.8 |
| Mannitol 27.7 mg + L Alanine 6.9 mg Na$_2$HPO$_4$ 21 mM | 8.04 | 8.06 | 8.03 | 8.00 | 28.7(*) | 23.0 | 31.2(*) | 20.5 | 2.1 |

(*)The titre does not vary significantly over time given the precision of the assay method (±10%)

EXAMPLE 9:
Results of stability of the freeze-dried products of urate oxidase at 30 EAU/vial at time 1 month at 35° C. and at time 3 months at 5° C., 25° C. and 35° C.

| | RECONSTITUTED SOLUTION | | | | | | | | |
|---|---|---|---|---|---|---|---|---|---|
| | CLARITY European Pharmacopoeia | | | | COLOUR European Pharmacopoeia | | | | |
| | | 1 month | 3 months | | | 1 month | 3 months | | |
| COMPOSITION | t = 0 | 35° C. | 5° C. | 25° C. | t = 0 | 35° C. | 5° C. | 25° C. | 35° C. |
| Na$_2$HPO$_4$ 40 mM Alanine 14.15 mg Mannitol 14.15 mg | I-II | =IV | I-II | +II | colourless | colourless | colourless | colourless | colourless |
| Na$_2$HPO$_4$ 40 mM Alanine 15.9 mg Mannitol 10.6 mg | I-II | II-III | <I | =I | colourless | colourless | colourless | colourless | colourless |
| Na$_2$HPO$_4$ 40 mM Alanine 16 mg Mannitol 7.3 mg | I-II | III-IV | =I | <I | colourless | colourless | colourless | colourless | colourless |
| Na$_2$HPO$_4$ 40 mM Alanine 18.9 mg Mannitol 4.72 mg | I-II | <IV | <I | I-II | colourless | colourless | colourless | colourless | colourless |
| Na$_2$HPO$_4$ 40 mM Alanine 20 mg Mannitol 2.5 mg | II-III | <IV | II-III | >IV | colourless | colourless | colourless | colourless | colourless |

| | pH OF THE RECONSTITUTED SOLUTION | | | | | ENZYMATIC ACTIVITY EAU/vial | | | |
|---|---|---|---|---|---|---|---|---|---|
| | | 1 month | 3 months | | WATER | | 1 month | 3 months | |
| COMPOSITION | t = 0 | 35° C. | 5° C. | 25° C. | CONTENT | t = 0 | 35° C. | 5° C. | 25° C. |
| Na$_2$HPO$_4$ 40 mM Alanine 14.15 mg Mannitol 14.15 mg | 8.01 | 8.01 | 8.04 | 8.02 | — | 30.3(*) | 23.2 | 29.8(*) | 30.5(*) |
| Na$_2$HPO$_4$ 40 mM Alanine 15.19 mg Mannitol 10.6 mg | 8.00 | 7.97 | 8.02 | 8.01 | — | 29.7(*) | 28.9(*) | 30.9(*) | 29.8(*) |
| Na$_2$HPO$_4$ 40 mM Alanine 16 mg Mannitol 7.3 mg | 7.99 | 7.98 | 8.02 | 8.00 | 2.0% | 29.2(*) | 26.8(*) | 30.3(*) | 30.0(*) |
| Na$_2$HPO$_4$ 40 mM Alanine 18.9 mg Mannitol 4.72 mg | 7.96 | 7.94 | 7.97 | 7.96 | — | 30.1(*) | 20.5 | 30.1(*) | 30.5(*) |
| Na$_2$HPO$_4$ 40 mM Alanine 20 mg Mannitol 2.5 mg | 7.96 | 7.93 | 7.96 | 7.95 | — | 29.4(*) | 17.9 | 29.4(*) | 25.7 |

(*)The titre does not vary significantly over time given the precision of the assay method (±10%)

We claim:

1. A formulation which is stable, freeze-dried, and pharmaceutically acceptable comprising a protein, a buffer, alanine, and mannitol, in which the mass ratio of mannitol to alanine ranges from 0.1 to 1.

2. The formulation according to claim 1, wherein the alanine is in crystallized form and the mannitol is in amorphous form.

3. An injectable solution comprising the formulation of claim 1, reconstituted with a pharmaceutically acceptable solvent.

4. The formulation according to claim 1, in which the protein is a hormone, an enzyme, or a cytokine.

5. The formulation according to claim 4, wherein the buffer is a phosphate buffer.

6. The injectable solution comprising the formulation of claim 4, reconstituted with a pharmaceutically acceptable solvent.

7. A process for the preparation of an injectable solution designed for subcutaneous, intravenous, or intramuscular injection into humans or animals comprising the step of dissolving the formulation according to claim 1, before use, in a pharmaceutically acceptable sterile solvent optionally containing an antibacterial preservative.

8. The process according to claim 7, wherein the pharmaceutically acceptable sterile solvent is selected from the group consisting of distilled water, an aqueous solution of 0.9% sodium chloride, an aqueous solution of 5% glucose, and a mixture thereof.

9. The process according to claim 7, wherein the antibacterial preservative is selected from the group consisting of benzylalcohol, phenol, and metacresol.

10. A formulation which is stable, freeze-dried, and pharmaceutically acceptable, comprising a protein selected from the group consisting of human growth hormone, urate oxidase, and interleukin-13, a buffer, alanine and mannitol, in which the mass ratio of mannitol to alanine ranges from 0.1 to 1.

11. The injectable solution comprising the formulation of claim 10, reconstituted with a pharmaceutically acceptable solvent.

12. A process for cryoprotecting a protein in a freeze-dried pharmaceutically acceptable formulation comprising the steps of combining a protein, a buffer, alanine, and mannitol, the mass ratio of mannitol to alanine ranging from 0.1 to 1; dissolving the mixture to form a solution; filtering the solution to effect a filtrate; and freeze-drying the filtrate.

13. The process according to claim 12, wherein the buffer is a phosphate buffer.

14. The process according to claim 12, wherein the protein is selected from the group consisting of human growth hormone, urate oxidase, and interleukin-13.

* * * * *